United States Patent
Zemp

(10) Patent No.: US 12,343,208 B2
(45) Date of Patent: Jul. 1, 2025

(54) ULTRASOUND IMAGING USING A BIAS-SWITCHABLE ROW-COLUMN ARRAY TRANSDUCER

(71) Applicant: Roger Zemp, Edmonton (CA)

(72) Inventor: Roger Zemp, Edmonton (CA)

( * ) Notice: Subject to any disclaimer, the term of this patent is extended or adjusted under 35 U.S.C. 154(b) by 211 days.

(21) Appl. No.: 17/941,341

(22) Filed: Sep. 9, 2022

(65) Prior Publication Data
US 2023/0083086 A1    Mar. 16, 2023

Related U.S. Application Data

(60) Provisional application No. 63/242,339, filed on Sep. 9, 2021.

(51) Int. Cl.
| | | |
|---|---|---|
| *A61B 8/00* | (2006.01) | |
| *G01S 7/52* | (2006.01) | |
| *G01S 15/89* | (2006.01) | |
| *G06T 5/20* | (2006.01) | |

(Continued)

(52) U.S. Cl.
CPC ............ *A61B 8/4488* (2013.01); *A61B 8/481* (2013.01); *A61B 8/5269* (2013.01); *G01S 7/52046* (2013.01); *G01S 15/8988* (2013.01); *G06T 5/20* (2013.01); *G06T 5/50* (2013.01); *G06T 5/77* (2024.01); *G06T 2207/10136* (2013.01);

(Continued)

(58) Field of Classification Search
CPC ..... A61B 8/4488; A61B 8/481; A61B 8/5269; G01S 7/52046; G06T 2207/10136; G06T 2207/20216; G06T 2207/30104
See application file for complete search history.

(56) References Cited

U.S. PATENT DOCUMENTS

| | | |
|---|---|---|
| 4,425,525 A | 1/1984 | Smith et al. |
| 4,448,075 A | 5/1984 | Takemura |
| 4,580,451 A | 4/1986 | Miwa |

(Continued)

FOREIGN PATENT DOCUMENTS

WO    2008/033528 A3    3/2008

OTHER PUBLICATIONS

Rasmussen, M. F., & Jensen, J. A.; 3-D ultrasound imaging performance of a row-column addressed 2-D array transducer: A measurement study; IEEE International Ultrasonics Symposium (IUS); Jul. 2013; pp. 1460-1463.

(Continued)

*Primary Examiner* — Joel F Brutus
(74) *Attorney, Agent, or Firm* — Nathan V. Woodruff

(57) ABSTRACT

An ultrasonic image is obtained from a bias-switchable row-column array transducer. A row channel data set is obtained by applying a bias voltage pattern to groups of row electrodes, the bias voltage pattern being chosen such that row electrodes within each group have the same bias voltage; transmitting a waveform along each of the plurality of row electrodes; and recording received column signals from each of the plurality of column electrodes. A column channel data set is obtained by applying a bias voltage pattern to groups of column electrodes, the bias voltage pattern being chosen such that column electrodes within each group have the same bias voltage; transmitting a waveform along each of the plurality of column electrodes; and recording received row signals from each of the plurality of row electrodes.

20 Claims, 12 Drawing Sheets

(51) Int. Cl.
   *G06T 5/50*  (2006.01)
   *G06T 5/77*  (2024.01)
(52) U.S. Cl.
   CPC ............... *G06T 2207/20216* (2013.01); *G06T 2207/30104* (2013.01)

(56) References Cited

U.S. PATENT DOCUMENTS

| | | | |
|---|---|---|---|
| 4,671,293 | A | 6/1987 | Shaulov |
| 5,027,820 | A | 7/1991 | Pesque |
| 5,152,294 | A | 10/1992 | Mochizuki |
| 5,327,895 | A | 7/1994 | Hashimoto |
| 5,345,139 | A | 9/1994 | Gururaja |
| 5,410,205 | A | 4/1995 | Gururaja |
| 5,460,179 | A | 10/1995 | Okunuki |
| 5,460,181 | A | 10/1995 | Seyed-Bolorforosh |
| 5,488,956 | A | 2/1996 | Bartelt |
| 5,490,512 | A | 2/1996 | Kwon et al. |
| 5,657,295 | A | 8/1997 | Howard |
| 5,671,746 | A | 9/1997 | Dreschel |
| 5,846,201 | A | 12/1998 | Adams |
| 6,381,197 | B1 | 4/2002 | Savord |
| 6,419,633 | B1 | 7/2002 | Robinson |
| 7,087,023 | B2 | 8/2006 | Daft |
| 7,544,165 | B2 | 6/2009 | Mamayek |
| 7,618,373 | B2 | 11/2009 | Ladabaum |
| 7,780,597 | B2 | 8/2010 | Panda |
| 9,285,466 | B2 * | 3/2016 | Gomersall .......... G01S 7/52077 |
| 2005/0043624 | A1 | 2/2005 | Oliver |
| 2007/0079658 | A1 | 4/2007 | Wagner |
| 2007/0206193 | A1 | 9/2007 | Pesach |
| 2009/0079299 | A1 * | 3/2009 | Bradley .............. G01S 15/8927 310/322 |
| 2009/0112095 | A1 * | 4/2009 | Daigle ................. A61B 8/4483 600/454 |
| 2009/0299184 | A1 * | 12/2009 | Walker ................. G10K 11/346 600/447 |
| 2010/0239133 | A1 | 9/2010 | Schmitt et al. |
| 2011/0054292 | A1 | 3/2011 | Hirson |
| 2014/0117809 | A1 | 5/2014 | Zemp |
| 2017/0337682 | A1 * | 11/2017 | Liao ..................... A61B 5/7267 |
| 2018/0146949 | A1 | 5/2018 | Nakamura |
| 2018/0164418 | A1 | 6/2018 | Zemp |
| 2019/0216421 | A1 * | 7/2019 | Hamilton ................ A61B 8/06 |
| 2019/0235077 | A1 | 8/2019 | Zemp et al. |
| 2020/0041644 | A1 | 2/2020 | Brown et al. |
| 2020/0305840 | A1 * | 10/2020 | Sboros ...................... G06T 7/73 |
| 2021/0302575 | A1 | 9/2021 | Twama |

OTHER PUBLICATIONS

Sampaleanu, A., Zhang, P., Kshirsagar, A., Moussa, W., & Zemp, R. J.; Top-orthogonal-to-bottom-electrode (TOBE) CMUT arrays for 3-D ultrasound imaging; IEEE transactions on ultrasonics, ferroelectrics, and frequency control; 2014; 61(2); pp. 266-276.

Wang, Y., Guo, Z., Wang, L. V., Erpelding, T. N., Jankovic, L., Robert, J. L., & David, G.; In vivo three-dimensional photoacoustic imaging based on a clinical matrix array ultrasound probe; Journal of Biomedical Optics; 2012; 17(6); p. 061208.

Ephrat, P., Keenlislide, L., Seabrook, A., Prato, F. S., & Carson, J. J.; Three-dimensional photoacoustic imaging by sparse-array detection and iterative image reconstruction; Journal of Biomedical Optics; 2008; 13(5); p. 054052.

Chee, R. K., Sampaleanu, A., Rishi, D., & Zemp, R. J.; Top orthogonal to bottom electrode (TOBE) 2-D CMUT arrays for 3-D photoacoustic imaging; IEEE transactions on ultrasonics, ferroelectrics, and frequency control; 2014; 61(8); pp. 1393-1395.

C. Ceroici et al., "3D photoacoustic imaging using Hadamard-bias encoding with a crossed electrode relaxor array," Opt. Lett., vol. 43, No. 14, pp. 3425-3428, 2018.

K. Latham, C. Ceroici, C. A. Samson, R. J. Zemp, and J. A. Brown, "Simultaneous azimuth and Fresnel elevation compounding: A fast 3-D imaging technique for crossed-electrode arrays," IEEE Trans. Ultrason., Ferroelectr., Freq. Control, vol. 65, No. 9, pp. 1657-1668, Jun. 2018.

C. Ceroici, T. Harrison, and R. J. Zemp, "Fast orthogonal row-column electronic scanning with top-orthogonal-to-bottom electrode arrays," IEEE Trans. Ultrason., Ferroelectr., Freq. Control, vol. 64, No. 6, pp. 1009-1014, Jun. 2017.

C. Ceroici, K. Latham, B. A. Greenlay, J. A. Brown, and R. J. Zemp, "Fast orthogonal row-column electronic scanning experiments and comparisons," IEEE Trans. Ultrason., Ferroelectr., Freq. Control, vol. 66, No. 6, pp. 1093-1101, Jun. 2019.

C. Ceroici, K. Latham, R. Chee, J. A. Brown, and R. J. Zemp, "Bias-sensitive crossed-electrode relaxor 2D arrays for 3D photoacoustic imaging," Proc. SPIE, vol. 10494, Feb. 2018, Art. No. 1049420.

Seo, Chi Hyung and Jesse T. Yen. "A 256×256 2-D array transducer with row-column addressing for 3-D rectilinear imaging." IEEE transactions on ultrasonics, ferroelectrics, and frequency control 56, No. 4 (2009): 837-847.

Novell, Anthony, Mathieu Legros, Jean-Marc Gregoire, Paul A. Dayton, and Ayache Bouakaz. "Evaluation of bias voltage modulation sequence for nonlinear contrast agent imaging using a capacitive micromachined ultrasonic transducer array." Physics in Medicine & Biology 59, No. 17 (2014): 4879.

\* cited by examiner

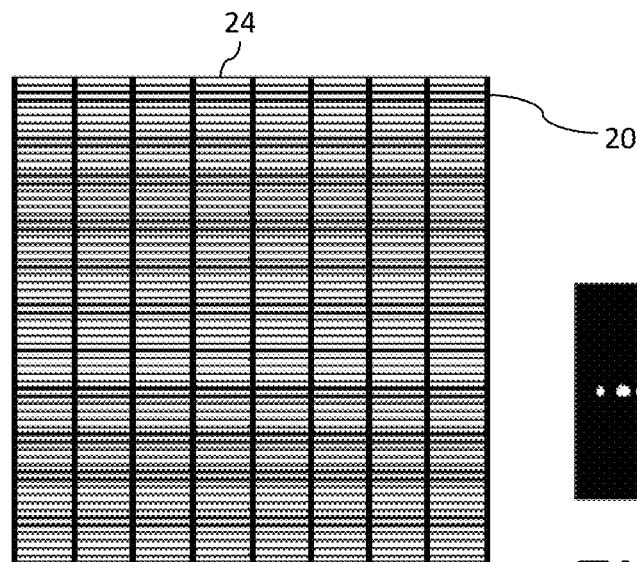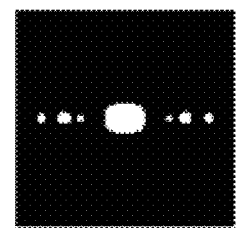
FIG. 5a  FIG. 5b
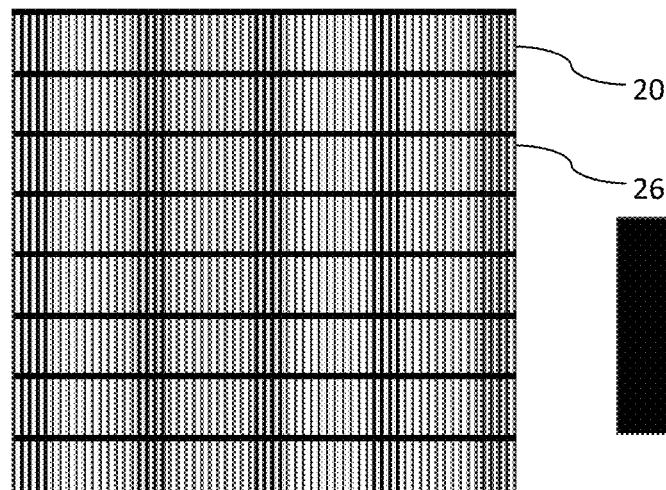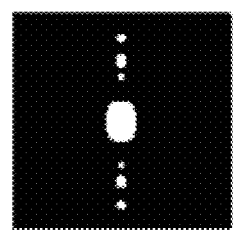
FIG. 5c  FIG. 5d

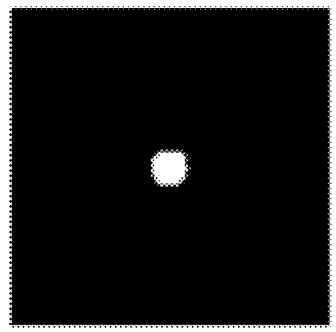
FIG. 6
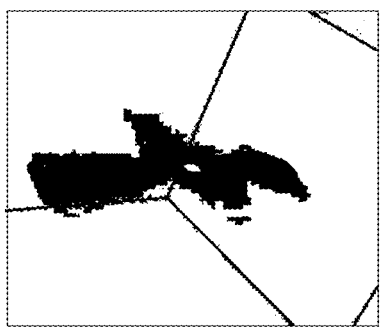 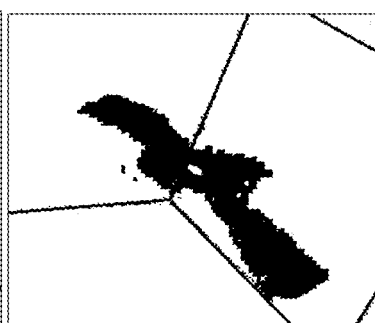 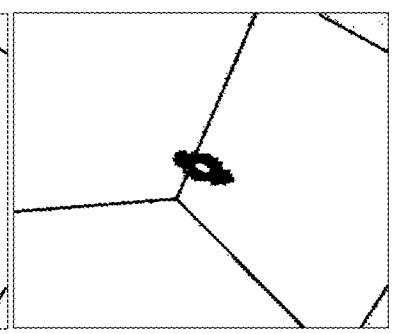
FIG. 7a   FIG. 7b   FIG. 7c

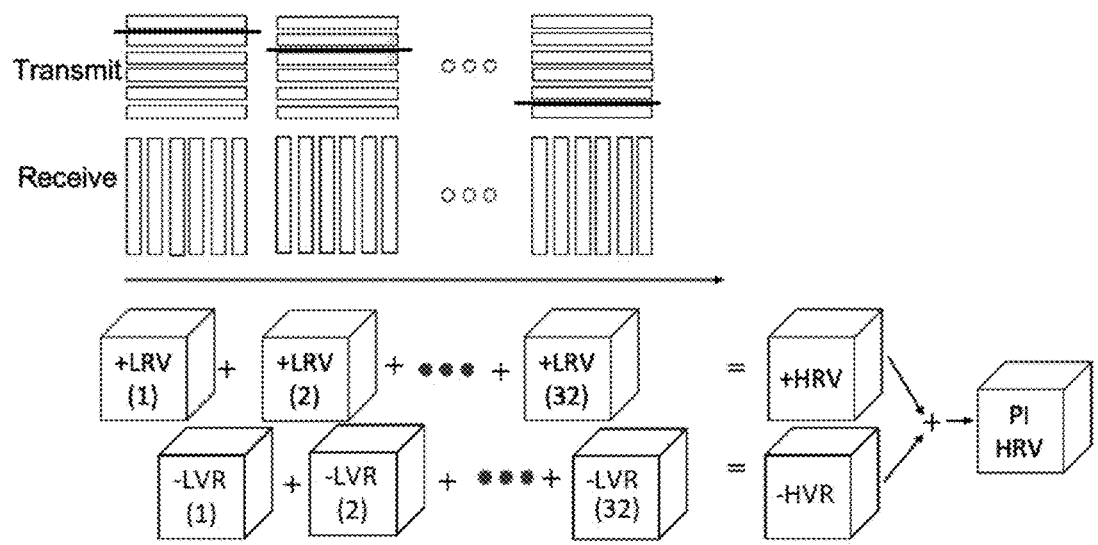
FIG. 12
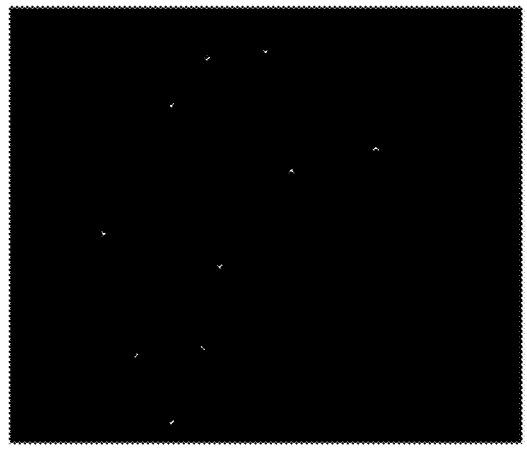
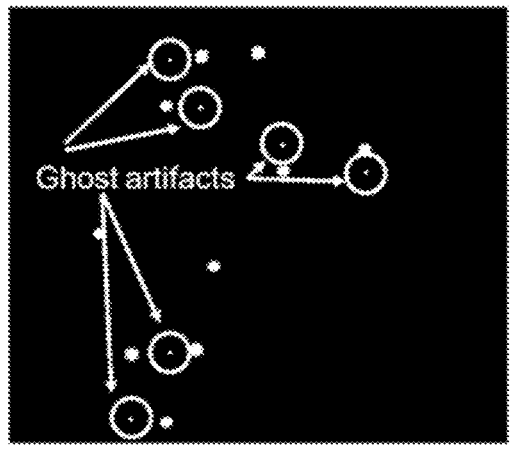
FIG. 13a   FIG. 13b

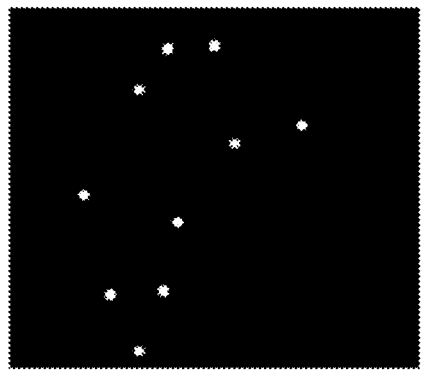 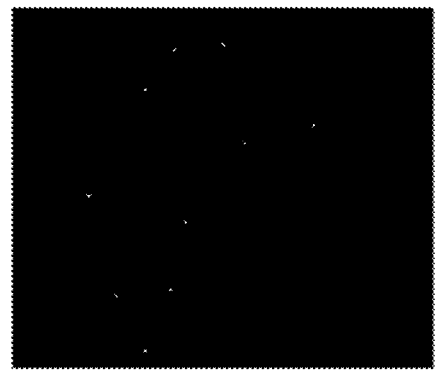
FIG. 14a  FIG. 14b
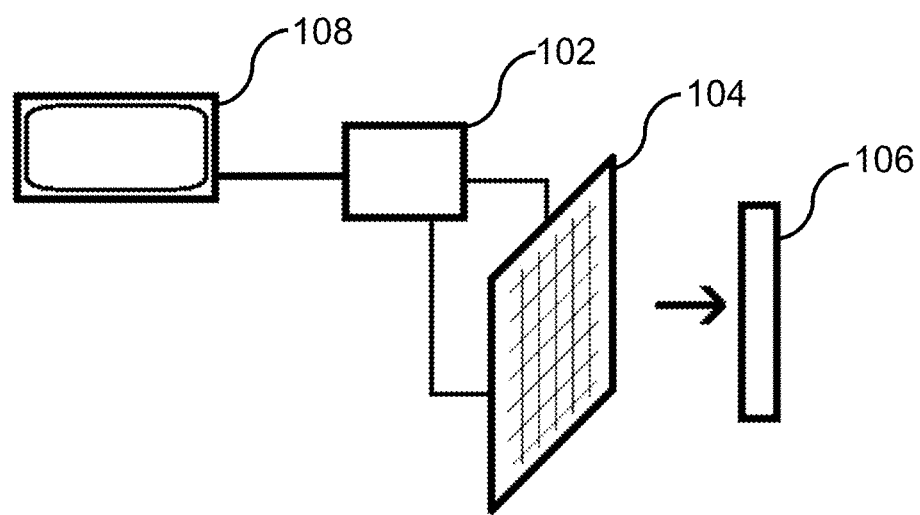
FIG. 15

ULTRASOUND IMAGING USING A BIAS-SWITCHABLE ROW-COLUMN ARRAY TRANSDUCER

TECHNICAL FIELD

This relates to ultrasound imaging using bias-switchable row-column arrays, also called top orthogonal to bottom electrode (TOBE) arrays.

BACKGROUND

Power Doppler Ultrasound is a method of imaging moving blood. Most Power Doppler ultrasound systems use 2D imaging with linear arrays, phased arrays, or convex arrays. 3D Power Doppler images can be formed using a sequence of 2D Power Doppler images by sweeping a 1D array transducer in the elevation direction or by using a 2D array. Other imaging approaches are known, such as color Doppler image, vector-flow image, strain image, or displacement-estimation image.

In conventional Power Doppler imaging, an ensemble of N pulses is fired down each line of sight, echo signals are wall-filtered (also referred to as clutter-filtered) to remove stationary echoes, then the power of moving blood signals is integrated over the ensemble to form a Power Doppler image. This is speed-limited by the acoustic propagation time in tissue. A newer approach is to use ultrafast Power Doppler, where a wide-field of view is insonicated using plane- or diverging waves, then receive echoes are focused everywhere in the image. Plane-wave or diverging wave compounding can improve spatial resolution, contrast, and signal-to-noise using this approach. The advantage of such ultrafast imaging schemes is that an image can be formed from each transmit event or from a small number of transmit events, leading to high frame rates and consequently long Doppler ensemble sizes. The long ensemble sizes lead to greatly improved sensitivity to slow bloodflow. However, extension of ultrafast Power Doppler to 3D has been challenging. Matrix probes with integrated microbeam formers do not currently support such ultrafast imaging modes. Fully-wired matrix probes have been limited to 32×32 arrays with poor image quality. Recently row-column arrays have been considered for 2D and 3D power Doppler, including schemes such as orthogonal plane-wave compounding. However, these approaches result in non-ideal focusing and undesirable artifacts in point-spread functions.

SUMMARY

According to an aspect, there is provided a method for ultrasound imaging using a bias-switchable row-column array transducer having a plurality of row electrodes and a plurality of column electrodes that are not parallel to the row electrodes, the method comprising: performing a one or more row transmit events, each transmit event comprising: identifying groups of row electrodes within the plurality of row electrodes, applying a bias voltage pattern to the groups of row electrodes, the bias voltage pattern being chosen such that rows within each group of row electrodes have the same bias voltage, transmitting a waveform along each of the plurality of row electrodes, and recording received column signals from each of the plurality of column electrodes, obtaining a row channel dataset for each of the groups of row electrodes using the received column signals from each of the one or more row transmit events, performing a column imaging sequence having one or more transmit events, each transmit event comprising: identifying groups of column electrodes within the plurality of column electrodes, applying a bias voltage pattern to the groups of column electrodes, the bias voltage pattern being chosen such that columns within each group of column electrodes have the same bias voltage, transmitting a waveform along each of the plurality of column electrodes, and recording received row signals from each of the plurality of row electrodes, obtaining a column channel dataset for each of the groups of column electrodes using the received row signals, and generating an ultrasonic image based on the row channel data set and the column channel dataset.

According to other aspects, the method may comprise one or more of the following aspects, alone or in combination: the groups of rows may comprise multiple, adjacent rows; for each of the row imaging sequence and the column imaging sequence, the bias voltage patterns may be derived from a row or a column of an invertible matrix, and the invertible matrix may be a Hadamard matrix and/or a scalar; the bias voltage pattern may comprise positive biases and negative biases, and the waveforms being sent to the row or column electrodes may have a negative bias are inverted copies of the waveforms sent to the row or column electrodes having a positive bias; the waveforms may be scaled or delayed relative to one another; the method may further comprise the step of generating a row image from the row channel dataset, and a column image from the column channel data set; generating an ultrasonic image may comprise combining the row image and the column image; the method may further comprise obtaining a plurality of row data sets and a plurality of channel data sets, the corresponding row images and column images being combined and averaged to obtain a combined ultrasonic image; the row images and column images may be combined and averaged using phase information; the method may further comprise the step of applying temporal or spatio-temporal filtering over the plurality of row datasets and the plurality of channel data sets; the step of generating an ultrasonic image may comprise applying a ghost artifact removal algorithm; the ultrasonic image may be a three-dimensional power Doppler image, a color Doppler image, vector-flow image, strain image, or displacement-estimation image; the waveforms in a transmit event may be configured to produce one of a plane wave, a cylindrically-diverging wave, or a cylindrically-converging wave; the step of generating an ultrasonic image may comprise applying a wall-filtering operation; the wall-filtering operation may be an infinite impulse response filter, a finite impulse response filter, an eigenfilter, or a singular value decomposition filter; the method may further comprise the step of inputting the ultrasonic image into an algorithm for rendering, the algorithm for rendering comprising a generative adversarial network or cycle-consistent generative adversarial network trained on paired or unpaired data from another imaging modality; the method may further comprise the step of injecting ultrasound contrast agents into a specimen to be imaged, and may further comprise the step of performing centroid localization of contrast agent signatures in the ultrasonic image, and may further comprise the step of repeatedly performing centroid localization of contrast agent signatures to obtain a plurality of super-localization images, and the plurality of super-localization images being combined to form a super-resolution ultrasound image or a velocity image.

According to an aspect, there is provided A system for ultrasound imaging comprising: an array transducer having a plurality of row electrodes and a plurality of column electrodes that are not parallel to the row electrodes, the plurality of row electrodes being separated from the column electrodes by a dielectric layer, a voltage source, a signal generator, a controller comprising a processing unit, the controller and/or the processing unit being programmed with instructions to: perform one or more row transmit events, each transmit event comprising: identifying groups of row electrodes within the plurality of row electrodes, applying a bias voltage pattern to the plurality of row electrodes, the bias voltage pattern being applied such that groups of row electrodes of the plurality of row electrodes have the same bias voltage, transmitting a waveform along each of the plurality of row electrodes, and recording received column signals from each of the plurality of column electrodes obtaining a row channel dataset for each of the groups of row electrodes using the received column signals, perform one or more column transmit events, each transmit event comprising: identifying groups of column electrodes within the plurality of column electrodes, applying a bias voltage pattern to the plurality of column electrodes, the bias voltage pattern being applied such that groups of column electrodes of the plurality of column electrodes have the same bias voltage, transmitting a waveform along each of the plurality of column electrodes, and recording received row signals from each of the plurality of row electrodes, obtaining a column channel dataset for each of the groups of column electrodes using the received row signals, and generating an ultrasonic image based on the row channel data set and the column channel dataset.

According to an aspect, there is provided a 3D ultrasonic imaging system using TOBE arrays, which may support high-resolution, ultrafast, 3D Power Doppler imaging, color Doppler image, vector-flow image, strain image, or displacement-estimation image, by applying a small set of biasing patterns and transmitting on columns while receiving on rows to form a so-called row-acquired image with fine resolution in elevation but poor focusing in azimuth, then switching roles of rows and columns to form a column-acquired image with poor elevation focusing but high-resolution azimuthal focusing. Row-acquired and column-acquired 3D images are then multiplied or combined and may be compounded over an ensemble size. Plane-wave or diverging wave compounding may be used to further improve contrast and resolution. High-resolution and high contrast images may be achieved, which may enable ultra-sensitive, ultrafast 3D imaging. A related method for 3D super-resolution imaging may use bias-switchable row-column arrays. Super-resolution ultrasound may be achieved in 2D by using ultrafast ultrasound imaging and super-localizing ultrasound contrast agents over many acquisitions. Row-acquisition multiplied by column-acquisition images may enable rapid 3D imaging with super-localization.

According to certain aspects, resolution, contrast, and imaging speed, may be improved via a method whereby an imaging sequence with highly anisotropic 3D point-spread function $PSF_r$ is used to acquire images with signal collection along rows, being focused in the elevation direction but poorly focused or unfocused in azimuth. Next, the roles of rows and columns are reversed so that signals are collected with columns, yielding associated point-spread function $PSF_c$. Compounding and/or cylindrical transmit focusing may improve focusing in the direction orthogonal to data collection. Under an approximation of local shift-invariance, the beamformed RF/IQ 3D image can be written as $g_r = PSF_r * f + n$, where $f$ is the object function and n is electronic noise. If the temporal autocorrelation at a location is $R_f(x,\tau)$ and the object scattering distribution is spatially uncorrelated, then the XPD image can be expressed as $XPD(x) = \langle \tilde{g}_r(x,t) \tilde{g}_c^*(x,t) \rangle = PSF_r(x)PSF_c(x) * \int S_f(x,\omega)d\omega$ where $\tilde{g}$ is the wall-filtered (or clutter-filtered) data, the ensemble average $\langle \cdot \rangle$ is approximated as a temporal average and $S_f$ is the object slow-time (wall-filtered) power spectral density. When flow is present with stationary tissue then only the scattered power of moving blood may be visualized. The effective PSF is now $PSF_r(x)PSF_c(x)$ which may be much more isotropic and focused compared to $PSF_r$ or $PSF_c$ alone. Resolution may be sacrificed in one direction at a time for imaging speed and still achieve fine effective isotropic focusing, and high contrast and imaging rates. Long ensembles may lead to improved SNR and sensitivity. $PSF_r(x)$ could be acquired using an unfocused plane wave transmission with elevational receive focusing, likewise for $PSF_r(x)$ but with azimuthal receive focusing. For a 5 MHz 128×128 lambda pitch array (~4×4 cm in size), with a 16 KHz PRF (pulse repetition frequency), and ensemble size of 50 using no Hadamard encoding orthogonal to the data acquisition direction, Hadamard encoded X-power doppler (HEX-PD) may be achieved at 160 PD Vol/s over volumes of 4×4×5 cm or larger with ~400 mm resolution. Sparse Hadamard bias encoding using 8 encodings per orientation should improve the signal to noise ratio (SNR), resolution, and contrast at the expense of speed (1000 3D-images/sec or 25 PD Vol/s (ensemble size 40) with >18 dB increase in SNR due to improved focusing). In contrast, most linear arrays may only achieve this frame-rate for 2D imaging, using an ensemble size of only ~10. Thus, several-fold improved sensitivity to blood flow compared to linear arrays may occur, a significant speedup in volumetric imaging speed compared to wobbled probes, and improvements in sensitivity, resolution, and imaging speed compared to MATRIX probes with integrated microbeam formers.

According to an aspect, there is provided a method for 3D ultrasound imaging using a bias-switchable row-column array transducer, the method of imaging involving a row-imaging sequence and a column imaging sequence multiplying the results and performing compounding, a row imaging sequence consisting of a set of transmit events as follows, which may be performed in a different functional order:

a. For each transmit event in a set of transmit events, apply row aperture encoding by applying a bias voltage pattern to row-electrodes or groupings of row electrodes derived from a row or column of an invertible matrix;

b. For each transmit event, sending transmit waveforms along these same rows, the waveforms being sent to electrodes having a negative bias voltage being inverted (and potentially scaled and delayed) copies of the waveforms sent to electrodes having a positive bias voltage;

c. After each transmit event, recording signals from column electrodes or a subset of such electrodes which are orthogonal to (or at least not parallel to) the biasing/transmitting electrodes;

d. After one or more transmit events, applying aperture decoding to obtain a channel-dataset from each element or groups of elements in the 2D array;

e. Implement 3D beamforming or image reconstruction using the decoded channel dataset;

f. Applying coherent compounding if multiple transmit waves are used.

A column imaging sequence may include a set of transmit events as follows:

a. For each transmit event, apply column aperture encoding by applying a bias voltage pattern to column-electrodes or groupings of column electrodes derived from a row or column of an invertible matrix;
b. For each transmit event, sending transmit waveforms along these same columns, the waveforms being sent to electrodes having a negative bias voltage being inverted (and potentially scaled and delayed) copies of the waveforms sent to electrodes having a positive bias voltage;
c. After each transmit event, recording signals from row electrodes or a subset of such electrodes which are orthogonal to (or at least not parallel to) the biasing/transmitting electrodes;
d. After one or more transmit events, applying aperture decoding to obtain a channel-dataset from each element or groups of elements in the 2D array;
e. Implement beamforming or image reconstruction using the decoded channel dataset;
f. Applying coherent compounding if multiple transmit waves are used.

After the row- and column-imaging sequences, the following steps may be taken:
reconstructing respective 3D beamformed images, applying a wall-filtering operation to remove stationary tissue echoes, multiplying the respective filtered reconstructed images (or the respective images associated with envelope-detection or absolute value operations) and repeating the above procedure multiple times. The product of the row- and column imaging sequence may then be averaged over the ensemble size to form a 3D image, such as a 3D power Doppler image, color Doppler image, vector-flow image, strain image, or displacement-estimation image, with improved resolution compared to either of the row- or columns reconstructed images alone.

In other aspects, the method may comprise one or more of the following features: the invertible matrix may be a Hadamard matrix; the entries from the invertible matrix may be assigned to groupings of rows or columns; the invertible matrix may be a scalar (1×1 matrix); the set of transmit signals for a given transmit event may be configured to produce a plane-wave (normally incident or tilting), a cylindrically-diverging wave, or a cylindrically-converging wave; the wall filtering operation may be an infinite impulse response filter, and finite impulse response filter, an eigenfilter, or filter based on singular-value decomposition of the Cassorati matrix; the bias-switchable row-column array transducer may be based on an electrostrictive composite; the bias-switchable row-column array transducer may be based on capacitive micromachined ultrasound transducers; the 3D image or its projection may be input into an algorithm for rendering such as a vesselness filter, segmentation algorithm or deep-learning-based algorithm, such a deep learning algorithm including a generative adversarial network or cycle-consistent generative adversarial network trained on paired or unpaired data from another imaging modality.

According to an aspect, there is provided a system for 3D ultrasound imaging, such as 3D power Doppler image, color Doppler image, vector-flow image, strain image, or displacement-estimation image, that includes a bias-switchable row-column array transducer, a set of biasing electronics, and pulsing-receiving electronics for a multiplicity of channels, as well as a controller and a processor or multiplicity of processors. The bias-switchable row-column array transducer may include: a dielectric sandwich layer which is will transduce a voltage to a force and a force to a voltage when a bias voltage is present, and which consists of a dielectric material or composite material consisting of multiple dielectric materials or a micromachined dielectric structure; electrically conductive top electrode strips in contact with the top surface of the dielectric sandwich layer; electrically-conductive bottom electrode strips orthogonal or at a substantially different angle than the top electrode strips and in contact with the bottom dielectric sandwich layer; an acoustically-absorbing backing layer or multiplicity of backing layers on the back-side of the array; an acoustic matching layer or multiplicity of matching layers on the front-side of the array. The controller may be configured to implement imaging involving a row-imaging sequence and a column imaging sequence, the processor reconstructing a 3D image for each. The processor may then be configured to multiplying the results and performing compounding. The controller may be configured to implement a row imaging sequence comprising the steps of the method described above.

According to an aspect, there is provided a method for 3D Ultrasound Contrast-Enhanced Super-Resolution Imaging using a bias-switchable row-column array transducer, the method of imaging comprising injecting ultrasound contrast agents, a row-imaging sequence and a column imaging sequence, filtering to remove stationary tissue components, ghost-artifact removal, multiplying the resulting filtered row-acquired and column-acquired images, performing centroid localization of contrast agent signatures; the row and column imaging sequence may comprise a set of transmit events according to the method steps described above. After the row- and column-imaging sequences, repeated multiple N times, temporal filtering or spatio-temporal filtering may be performed over the ensemble of such acquisition sequences to reject stationary tissue components, then multiplying the resulting row-acquired and column acquired 3D images, applying a ghost artifact removal algorithm, and applying a super-localization algorithm to estimate the centroid of each detected microbubble signature. The procedure may then be repeated to obtain super-localization images from sparse agents to form a super-resolution ultrasound angiography image. Amplitude modulation, pulse inversion, or super-harmonic strategies may be used to enhance the contrast-to-tissue signal of the contrast agents. Ghost artifacts ma be rejected by assessing if agent signatures exist vertically and horizontally from each detected signature and rejecting the weaker signals.

In other aspects, the features described above may be combined together in any reasonable combination as will be recognized by those skilled in the art.

BRIEF DESCRIPTION OF DRAWINGS

These and other features will become more apparent from the following description in which reference is made to the appended drawings, the drawings are for the purpose of illustration only and are not intended to be in any way limiting, wherein:

FIG. 5a is an inverse Hadamard matrix applied to a row-column array transducers with 8 groups of columns and 128 rows.

FIG. 5b is a row-acquired image produced by the array of FIG. 5a.

FIG. 5c is an inverse Hadamard matrix applied to a row-column array transducers with 128 columns and 8 groups of rows.

FIG. 5d is a column-acquired image produced by the array of FIG. 5c.

FIG. 6 is an image produced by combining the column-acquired and row-acquired images.

FIG. 7a shows an image of a point-spread function in a first direction

FIG. 7b shows an image of a point-spread function in a second direction

FIG. 7c shows an image of the combined images from FIGS. 7a and 7b.

FIG. 12 is a schematic of a row-column array used for imaging.

FIG. 13a is an example of an object function

FIG. 13b is an example of a super-localization output with ghost artifacts.

FIG. 14a is an example of a HEX-US image after ghost artifact removal.

FIG. 14b is an example of a super-localization output of an image.

FIG. 15 is a schematic diagram of an ultrasonic detection system.

DETAILED DESCRIPTION OF PREFERRED EMBODIMENTS

Figure 1A:
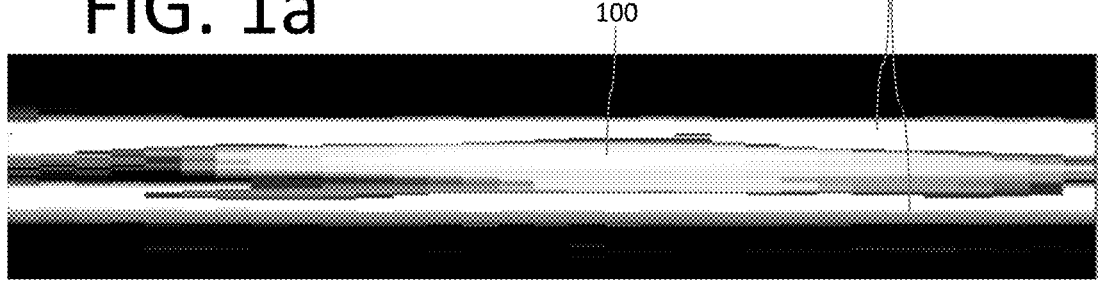
FIG. 1a through 1c are Power Doppler images of blood flow phantom 100 in a tube.
Figure 1B:
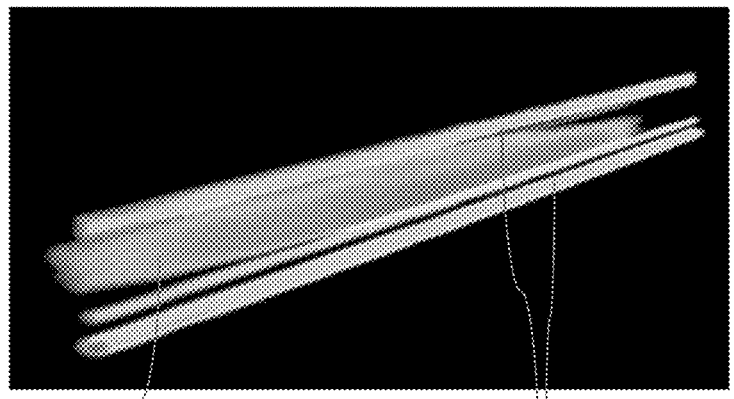
Figure 1C:
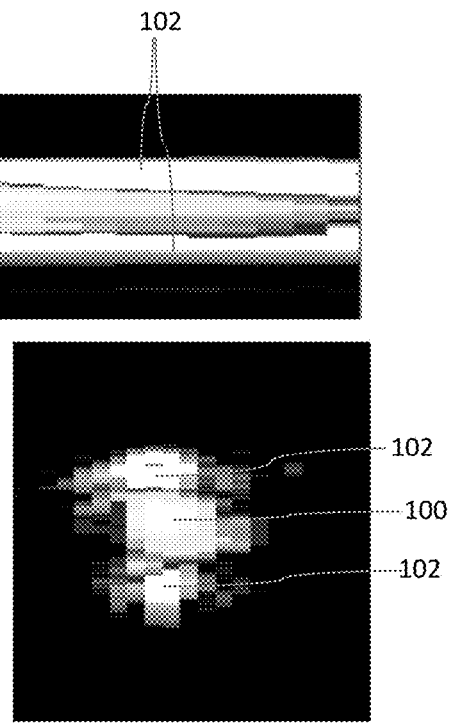

Ultrafast Volumetric 3D Imaging may be used to provide acoustic angiography. TOBE (top orthogonal to bottom electrodes) arrays could scale to large sizes providing widefield acoustic angiography. Ultrafast Power Doppler imaging, or other 3D imaging, with a row-column array may be obtained using orthogonal plane wave compounding. However, such an array may not be bias-switchable, resulting in undesirable imaging artifacts. It is also possible to reconstruct Power Doppler images by repeating image-plane acquisitions with a TOBE array using Scheme 1 (row column imaging without bias switching, including virtual line source imaging methods), or using Fast Orthogonal Row-Column Electronic Scanning (FORCES), Ultra-Fast Row Column Electronic Scanning (uFORCES), or Simultaneous Azimuthal and Fresnel Elevational (SAFE) compounding. FORCES, uFORCES, and SAFE compounding methods require a bias-switchable TOBE array. FIG. 1a through FIG. 1c are examples of Power Doppler images of blood flow phantoms 100 in a tube 102 using FORCES imaging. FIG. 1a, FIG. 1b, and FIG. 1c depict side, perspective, and end views, respectively. A limitation of these approaches is the imaging time needed (>1 sec/Vol). Using Scheme 1, out-of-plane resolution may be sub-optimal away from the transmit focus and if using diverging waves from a virtual line source, SNR may be poor. SAFE compounding and FORCES require a lot of coherent compounding, which may not work well with significant tissue/blood motion. FORCES and uFORCES have only one-way elevational focusing (but two-way in-plane focusing). uFORCES B-scanning may be faster than FORCES, with a requirement for coherent compounding over only a few sparse transmit events, but Power Doppler volumetric imaging is still relatively slow. A fast volumetric Power Doppler imaging method that may achieve high quality at thousands of frames per second may enable long ensemble times and thus high sensitivity.

Referring to FIG. 15, an ultrasonic imaging system may include a transducer array 100 connected to a controller 102. The transducer array 100 generates ultrasonic signals that are used to image a sample 104. In response to received signals, controller 102 generates an ultrasonic image, which may then be displayed on a display 106. Controller 102 may be a general purpose processor or other suitable computer device, and may include an internal storage device or may be connected to an external storage device. The image may be stored and transmitted to another device, may be displayed on an integrally formed display, remote display, personal electronic device, or the like.

Theory

3D Power Doppler

Signals may be recorded from every element of a bias-switchable row-column array with boosted SNR by using multiple Hadamard-based column biasing patterns while receiving from rows. It may take a long time to form a single image with this approach, and multiple images are needed in a Doppler ensemble to form a Power Doppler image. The discussion below may also apply to other 3D imaging schemes, such as color Doppler image, vector-flow image, strain image, or displacement-estimation image.

Let $g_r$ be the RF or IQ beamformed 3D image acquired using rows, for a potentially sparse channel aperture encoding. Under the approximation of a linear shift-invariant system, this can modeled as a convolution between an object function $f$ and point-spread function $PSF_r(x)$, along with additive electronic noise: $g_r(x,t) = PSF_r(x) * f(x,t) + n$.

The object function may change over time, as is the case with bloodflow and will be modelled as a zero-mean random process. A similar model can be developed for the data acquired with columns: $g_c(x,t) = PSF_c(x) * f(x,t) + n$.

Wall-filtering may be performed on the beamformed RF data, which will produce temporally-filtered outputs $\tilde{g}_r, \tilde{g}_c$ insensitive to stationary tissues. Given the object function may consist of stationary tissue $f_t$ and moving blood $f_b$ components: $f(x,t) = f_t(x) + f_b(x,t)$. Then, for example, $\tilde{g}_r \approx PSF_r(x) * f_b(x,t) + n$.

The power Doppler image acquired with TOBE row acquisition, $PD_r = \langle \tilde{g}_r \tilde{g}_r^* \rangle$, may have good elevational resolution, but may have poor azimuthal resolution. Likewise, the Power Doppler image $PD_c = \langle \tilde{g}_c \tilde{g}_c^* \rangle$ acquired with TOBE columns may have good azimuthal resolution, but may have poor elevational resolution. Here $\langle \cdot \rangle$ represents statistical ensemble averaging, which is approximated by slow-time averaging over a Doppler ensemble.

To achieve a power Doppler image with improved and more isotropic resolution, consider forming the image $XPD = \langle \tilde{g}_r \tilde{g}_c^* \rangle$. Expanding, we have $$XPD = \langle \tilde{g}_r \tilde{g}_c^* \rangle = \langle (PSF_r(x) * f(x,t) + n_r)(PSF_c(x) * f(x,t) + n_c)^* \rangle$$

Now since the object function and the noise are uncorrelated, and the noise acquired with row acquisition and column acquisition will be uncorrelated:

$$XPD \cong \langle (PSF_r(x) * f_b(x, t))(PSF_c(x) * f_b(x, t))^* \rangle ==$$

$$\left\langle \left( \int PSF_r(x') f_b(x - x', t) dx' \right) \left( \int PSF_c(x'') f_b(x - x'', t) dx'' \right)^* \right\rangle =$$

$$\int \int PSF_r(x') PSF_c(x'') \langle f_b(x - x', t) f_b^*(x - x'', t) \rangle dx' dx''$$

The object spatio-temporal autocorrelation $R_{ff}(x,x'|t,t') \equiv \langle f(x,t) f^*(x',t') \rangle$ may be modeled as temporally wide-sense stationary, and spatially statistically uncorrelated but spatially varying:

$$R_{ff}(x,x'|t,t') = R_f(x|t-t') \delta(x-x')$$

where $\delta$ is a delta function and $R_f(x|t-t') \equiv \langle f(x,t) f^*(x,t') \rangle$. Now in the above, $\langle f_b(x-x',t) f_b^*(x-x'',t) \rangle$ must be evaluated. This may be written as:

$$\langle f_b(x-x',t) f_b^*(x-x'',t) \rangle = R_b(x-x'|0) \delta(x''-x')$$

This then simplifies the integration as:

$$XPD \cong \int \int PSF_r(x') PSF_c(x'') R_b(x - x' \mid 0) \delta(x'' - x') dx' dx'' =$$

$$\int PSF_r(x'') PSF_c(x'') R_b(x - x'' \mid 0) dx'' =$$

$$PSF_r(x) PSF_c(x) * R_b(x \mid 0) = PSF_{rc}(x) * R_b(x \mid 0)$$

Here $PSF_{rc}(x) = PSF_r(x) PSF_c(x)$ is the new point-spread function, and may have more isotropic resolution compared to $PSF_r(x)$ or $PSF_c(x)$ alone.

Now a spatially-varying zero-temporal lag autocorrelation can be written as an integral over the power spectral density: $R_b(x|0) = \int S_b(x,f) df$. Thus, $$XPD \equiv PSF_{rc}(x) * \int S_b(x,f) df$$

and represents an image of the scattering power due to moving blood, as resolved by a point-spread function with improved isotropic resolution.

In practice, the system may not be linear shift-invariant, so the convolution model above may only be an approximation that is valid locally. However, numerical simulations may be used to validate the approach described herein. The advantage of the above approach is that row- and column-acquired images may be acquired quickly with sacrificed elevational or azimuthal resolutions, respectively, but the above approach can lead to high-quality volumetric power Doppler images in a rapid way.

Biasing and Pulsing Schemes to Implement HEX-Power Doppler

Figure 2A:
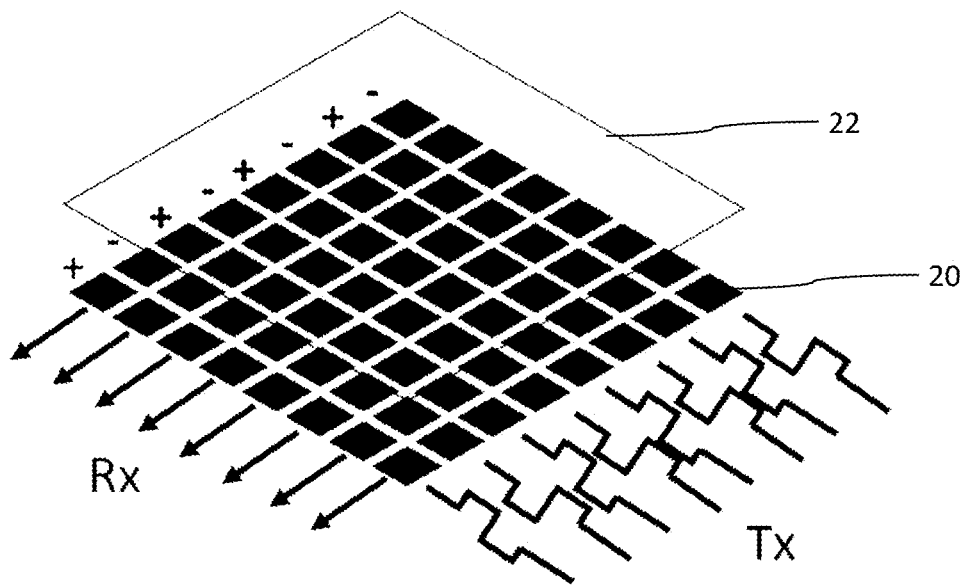
FIGS. 2a and 2b are perspective views of Hadamard bias patterns applied to an 8×8 row-column array.
Figure 2B:
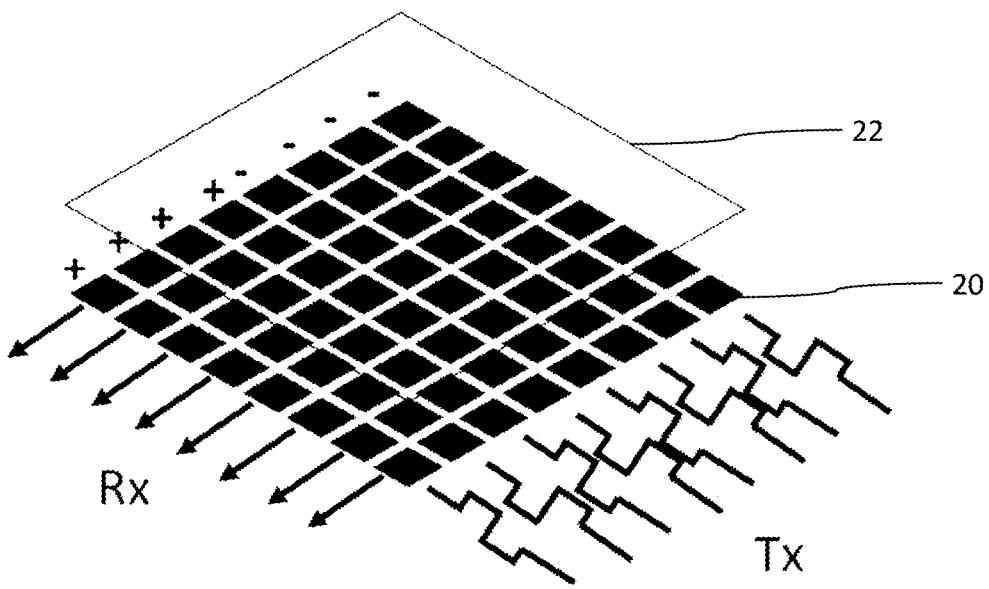

One simple way to read out from every element of a row-column array is to bias one column at a time while recording signals from every row. An alternative method is to apply Hadamard biasing patterns to columns while reading out signals from rows. After aperture decoding using an inverse Hadamard matrix, signals from every element of the array may be recovered, with improved signal-to-noise ratio compared to the approach of biasing one column at a time. FIG. 2a and FIG. 2b depict examples of first and second Hadamard bias patterns applied to an 8×8 row-column array transducer 20, that produce a plane wave 22 at a first angle.

Figure 3A:
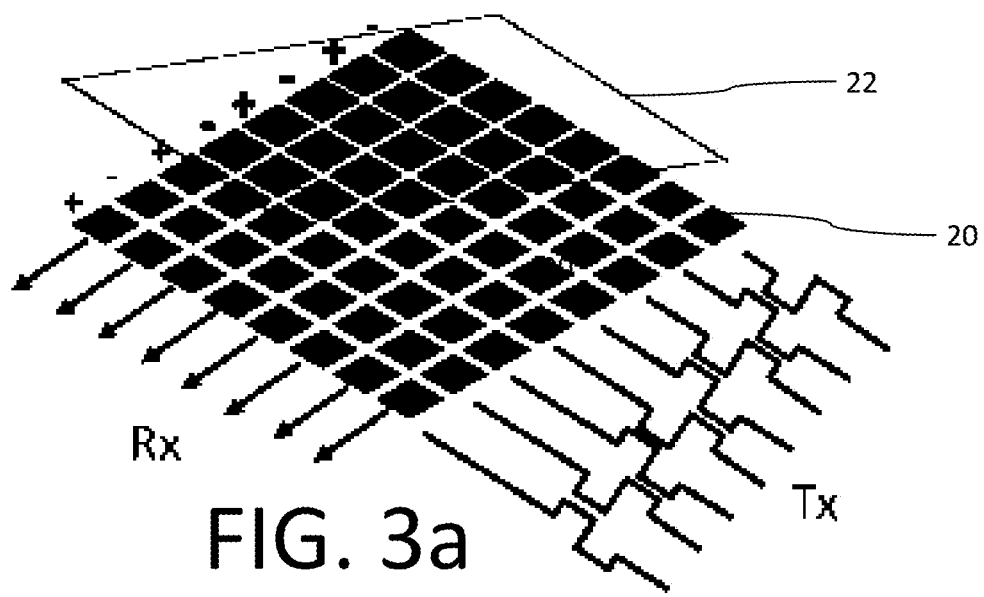
FIGS. 3a and 3b are perspective views of Hadamard bias patterns applied to an 8×8 row-column array with a linear delay profile applied to produce a plane wave at an angle.
Figure 3B:
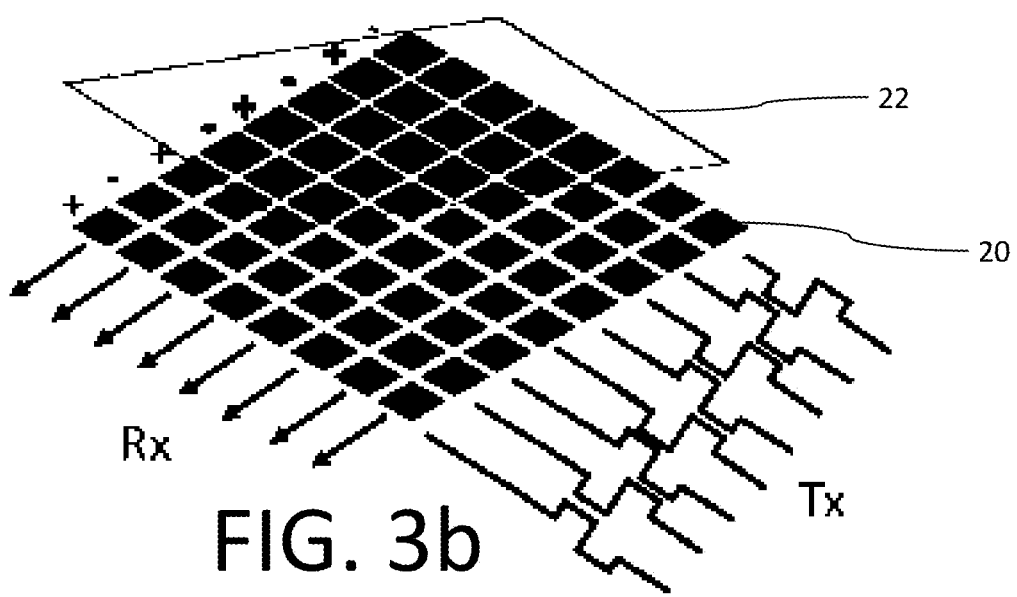

For larger row-column arrays, the time required for these approaches increases. Moreover, these approaches does not involve a transmission strategy. To achieve a widefield plane wave (or diverging wave) transmission, when columns are biased with a particular Hadamard biasing pattern, signals may be transmitted along columns. When a negative bias voltage is present the polarity of the transmit waveform may be inverted so that the emitted acoustic wave from that column is identical to the emitted wave from a column with a positive bias and a positive polarity transmit signal. When the delay for each column is constant, a normal plane wave emission may result. When a linear delay profile is applied, a tilted plane wave emission may result. FIG. 3a and FIG. 3b depict examples of a first and second Hadamard bias patterns applied to an 8×8 row-column array transducer 20 with a linear delay profile applied, that produce a plane wave 22 at a second angle.

Figure 4:
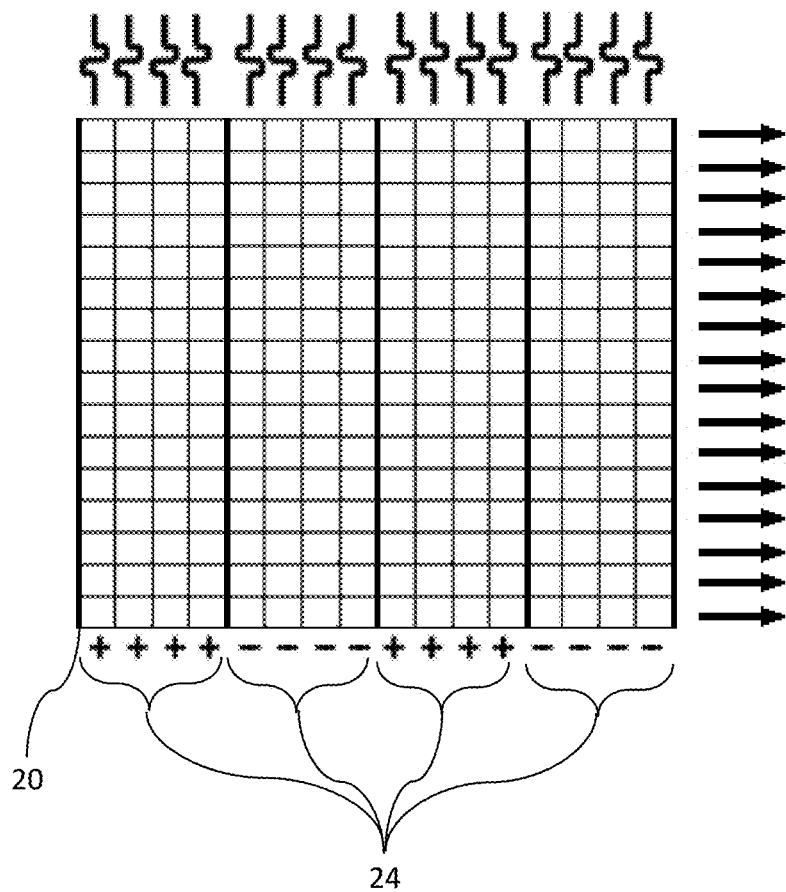
FIG. 4 depicts a row-column array with sixteen columns binned into groups of four columns.

To improve volumetric imaging speeds, columns (or rows) may be binned prior to bias encoding. In one example, shown in FIG. 4, a row-column array transducer 20 is shown with sixteen columns binned into four groups of columns 24 with four columns in each group. A bias pattern is applied to the groups of columns according to the second row of the following Hadamard Matrix:

$$H = \begin{bmatrix} 1 & 1 & 1 & 1 \\ 1 & -1 & 1 & -1 \\ 1 & 1 & -1 & -1 \\ 1 & -1 & -1 & 1 \end{bmatrix}$$

In another example, for a 128×128 array, if columns may be binned into 8 groups of 16, and bias patterns from an 8×8 Hadamard matrix are applied to the groupings, only 8 transmit events are needed, but with the consequence of reading out from an effective 8×128 array. This will result in poor azimuthal but excellent elevational focusing.

Other grouping schemes may be possible besides simple binning, and in different sizes or numbers. In addition, other bias patterns may also be used. The matrix may be invertible, and/or may be a scalar.

The bias voltage pattern may use positive biases and negative biases, where the waveforms sent to the row or column electrodes that have a negative bias are inverted copies of the waveforms sent to the row or column electrodes having a positive bias (or vice versa). The waveforms may be scaled or delayed relative to one another.

A single normal plane wave may be sufficient to achieve fine resolution but more plane wave compounding may improve contrast and resolution at the expense of imaging speed.

HEX-PD Simulations:

In one simulation, Field II was used to generate plane wave emissions and scattering data collected from elements of a Hadamard-bias-encoded TOBE array. The data was then reconstructed using a custom delay- and sum plane-wave beamforming algorithm accounting for a constant plane wave delay then a custom delay from a scatterer to each element of the array. 64×64 and 128×128 10 MHz lambda-pitch arrays were simulated.

The HEX-PD methodology is discussed below, along with some simulation results. Shift-invariant convolution-based models are shown first, and then some results of a shift-variant model are shown.

FIG. 5a depicts the application of an inverse Hadamard matrix for aperture decoding on row-column array transducer 20 with 8 groups of columns 24 and 128 rows; an example of a row-acquired image $g_r$ is shown in FIG. 5b. FIG. 5c depicts the application of an inverse Hadamard matrix for aperture decoding on row-column array transducer 20 with 128 columns and 8 groups of rows 26; an example of a column-acquired image $g_c$ is shown in FIG. 5d. FIG. 6 depicts the X-Power Doppler image $XPD=\langle \tilde{g}_r \tilde{g}_c^* \rangle$.

Referring to FIG. 7a through FIG. 7c, results of HEX-PD 3D PSF simulations with 10 MHz 128×128 TOBE array are shown. FIG. 7a shows $PSF_r$ with 8 transmission events, FIG. 7b shows $PSF_c$ with 8 transmission events, and FIG. 7c shows $PSF_r \times PSF_c$.

Figure 8A:
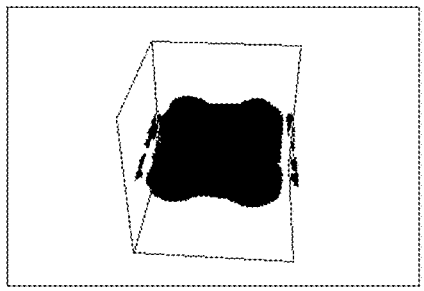
FIG. 8a shows a column-acquired image of blood vessels.
Figure 8B:
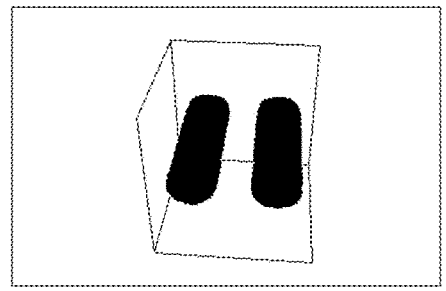
FIG. 8b shows an image of a combined column- and row-acquired image of blood vessels.
Figure 9A:
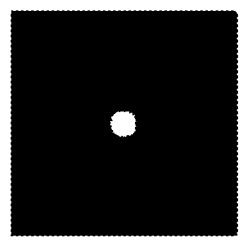
FIG. 9a shows a cross-sectional view of a blood vessel with an ensemble size of N=1
Figure 9B:
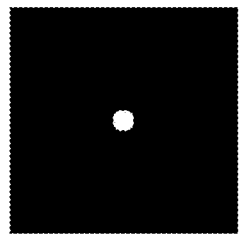
FIG. 9b shows a cross-sectional view of a blood vessel with an ensemble size of N=20.

Referring to FIG. 8a and FIG. 8b, results of HEX-PD 3D PSF simulations of blood vessels with 10 MHz 128×128 TOBE array are shown. FIG. 8a shows the column acquired image with 8×128 TOBE, 8 transmission events, and an ensemble size of N=10. FIG. 8b depicts the HEX-PD image using the column-acquired image and the row-acquired image (not shown). FIG. 9a and FIG. 9b show the effects of ensemble size and HEX-PD compounding. FIG. 9a depicts a blood vessel cross section with and ensemble size of N=1, and FIG. 9b depicts the same blood vessel cross section with an ensemble size of N=20.

Figure 9C:
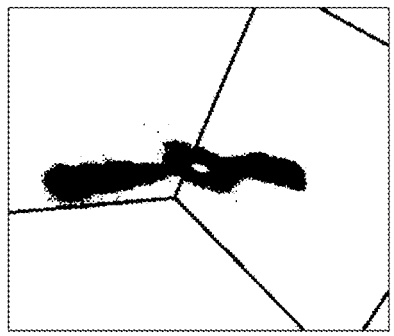
FIG. 9c through 9e depict images obtained along a first axis, a second axis, and by combining the first and second axes, with a single normal plane wave.
Figure 9D:
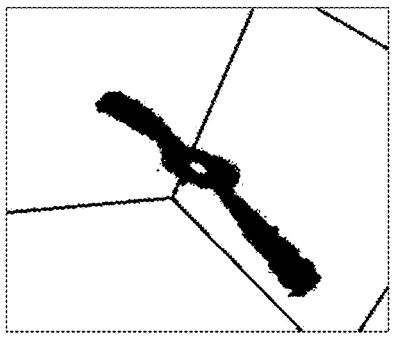
Figure 9E:
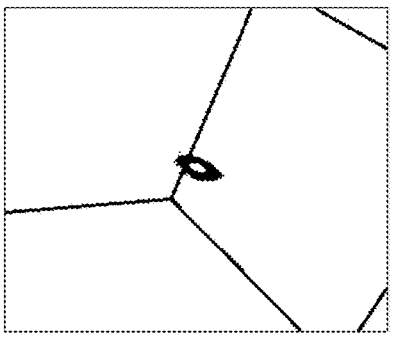
Figure 9F:
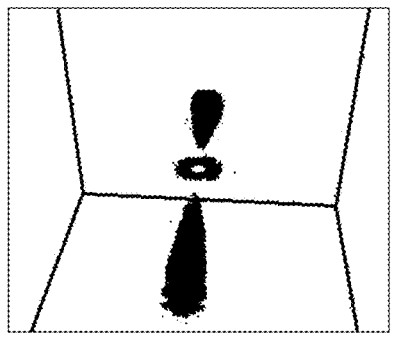
FIG. 9f through 9h depict images obtained along a first axis, a second axis, and by combining the first and second axes, with angled beams at −7, 0, and 7 degrees.
Figure 9G:
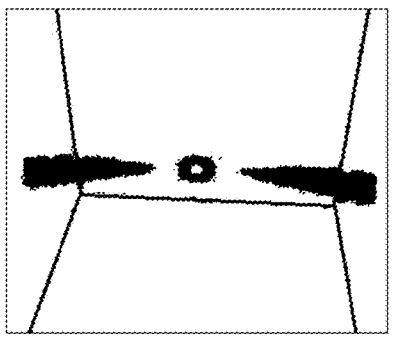
Figure 9H:
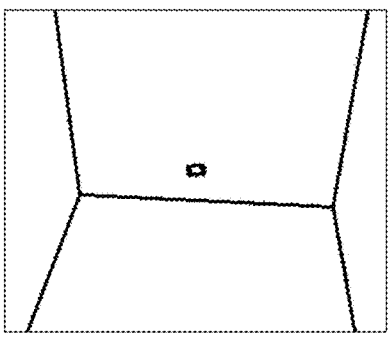

In some examples, plane wave compounding may be used, which may offer a slight advantage over imaging without plane wave compounding. FIG. 9a depicts a 2D image obtained with 1 plane wave per orientation, 16 transmission events per image, and coherent compounding over 8 transmission events. FIG. 9b depicts a 2D image obtained with 3 plane waves per orientation, 48 transmission events per image, and coherent compounding over 16 transmission events. FIG. 9c, FIG. 9d, and FIG. 9e depict a 3D $PSF_r$, $PSF_c$, and $PSF_r \times PST_c$ image, respectively, with a single normal plane wave. FIG. 9f, FIG. 9g, and FIG. 9h depict a 3D $PSF_r$, $PSF_c$, and $PSF_r \times PST_c$ image, respectively, with angled beams at −7, 0, and 7 degrees.

Figure 10A:
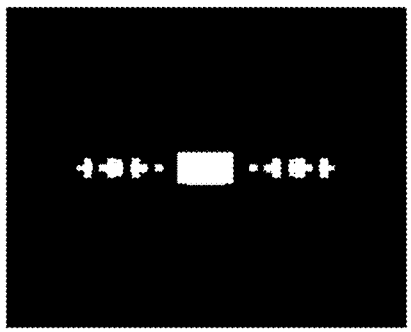
FIG. 10a through 10c depict images obtained using shift-invariant point-spread function models along a first axis, a second axis, and a combination of the first and second axes.
Figure 10B:
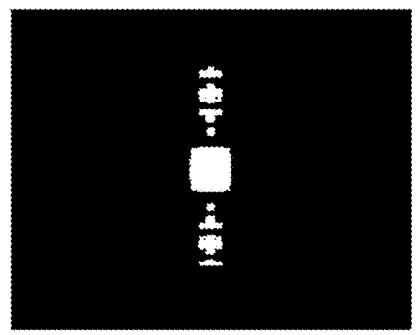
Figure 10C:
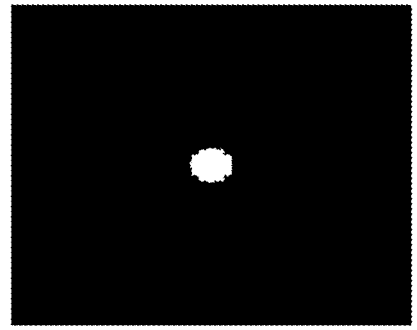
Figure 10D:
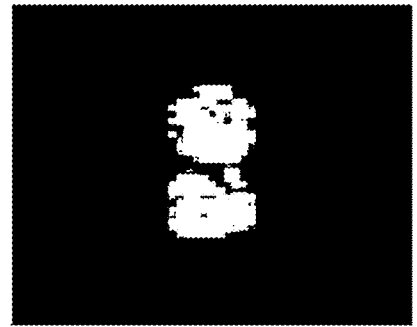
FIG. 10d depict a cross-sectional image of two blood vessels.
Figure 11A:
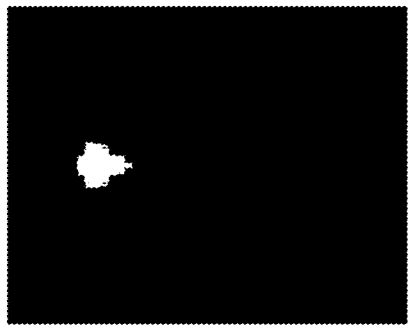
FIG. 11a through 11c depict images obtained using shift-invariant point-spread function models along a first axis, a second axis, and a combination of the first and second axes.
Figure 11C:
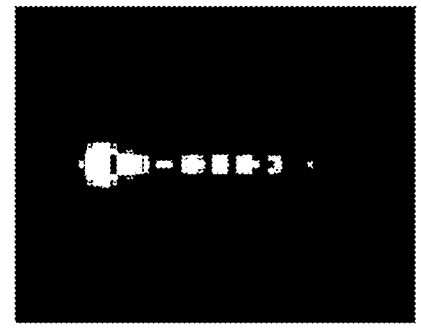
Figure 11B:
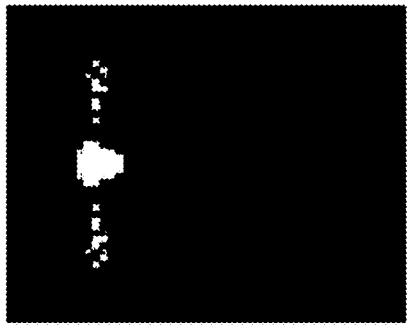
Figure 11D:
FIG. 11d depict a cross-sectional image of two blood vessels.

Table 1 below shows some potential HEX-PD volumetric imaging rates and sensitivities with examples of potential applications.

depict a second shift-variant simulation HEX-PD Shift-Variant Simulations with 64×64 10 MHz TOBE array, with a group size of 8 and a focal depth of 20 mm. FIG. 10a, FIG. 10b, and FIG. 10c depict a $PSF_r$, $PSF_c$, $PSF_r \times PSF_c$, and a blood vessel cross section image (N=10), respectively.

Super-Resolution Contrast Imaging

Super-resolution contrast ultrasound works by super-localizing microbubble contrast agent signals and accumulating their positions over an extended observation time. Ultrafast ultrasound localization microscopy for deep super-resolution vascular imaging.

A row-column array may be used for super-resolution imaging, however such an approach may require a non-bias-switchable array and a large number of transmit events to form a 3D image. This approach is shown in FIG. 12, in which N transmit events for an N×N array are required to form one 3D image. In contrast, the approach described herein may require only 16 transmit events for arrays of size 128×128 or even larger, and may achieve ultrafast imaging rates, leading to shortened image acquisition time. Moreover, because larger arrays can be used with high numerical aperture focusing, finer-resolution can be achieved prior to super-localization, meaning that agent distribution may not need to be as sparse, and thus lead to more super-localization image frames to accumulate for high quality and fast 3D super-resolution acoustic angiography.

Hadamard-Encoded X-Ultrasound (HEX-US) Super-Resolution Method

Hadamard-Encoded X-ultrasound imaging may be used to form ultrafast volumetric images of sparse contrast agents, perform artifact removal and super-localization in 3D over a large number of images to form a super-resolution acoustic angiography image.

When the object function of interest is contrast agents, $f_c(x,t)=\Sigma_i a_i \delta(x-x_i(t))$, then including tissue and blood, the total object function may be $f(x,t)=f_t(x)+f_b(x,t)+f_c(x,t)$, with $f_c >> f_b$. An example of an object function is shown in FIG. 13a. The product of dominant moving object function components may be defined as

TABLE 1

Potential HEX-PD volumetric imaging rates and sensitivities

| Array | PRF (KHz) | Res. (mm) | Field of view (cm) | Ensemble size | Volume Rate (Vol/s) | X Sensitivity vs traditional Doppler | Potential Application |
| --- | --- | --- | --- | --- | --- | --- | --- |
| 128 × 128, 5 MHz | 16 | 0.5 | 4 × 4 × 5 | 40 | 25 | 4 | Carotid |
| 1024 × 1024, 8 MHz | 16 | 0.2 | 16 × 16 × 4 | 1000 | 1 | 100 | Breast |
| 256 × 256, 30 MHz | 50 | 0.07 | 1.3 × 1.3 × 1 | 500 | 50 | 50 | Small animal |
| 48 × 64, 2.5 MHz | 5 | 1 | 10 × 10 × 15 | 30 | 3 | 3 | Cardiac |

Shift-Variant Simulations

The previous simulations relied on shift-invariant point-spread function models. The following simulation results include non-shift-varying models. X-Y image planes at a fixed 20 mm depth from a 64×64 10 MHz array.

FIG. 10a through FIG. 10d depict a first shift-variant simulation HEX-PD Shift-Variant Simulations with 64×64 10 MHz TOBE array, with a group size of 8 and a focal depth of 20 mm. FIG. 10a, FIG. 10b, and FIG. 10c depict a $PSF_r$, $PSF_c$, $PSF_r \times PSF_c$, and a blood vessel cross section image (N=10), respectively. FIG. 11a through FIG. 11d $$f_c(x,t) f_c^*(x',t) = \left(\sum_i a_i \delta(x-x_i(t))\right)\left(\sum_j a_j \delta(x'-x_j(t))\right) = \sum_i \sum_j a_i a_j \delta(x-x_i(t)) \delta(x'-x_j(t))$$

But the product of two delta functions is zero unless their arguments are identical so $f_c(x,t) f_c^*(x',t)=\Sigma_i \Sigma_j a_i a_j \delta(x-x_i(t)) \delta(x-x'-(x_i(t)-x_j(t)))$. The argument of the right delta function can be zero when i=j and x−x'=0 or when i≠j and x−x'−(x_i(t)−x_j(t))=0, so $$f_c(x, t)f_c^*(x', t) = \dfrac{\sum_i a_i^2 \delta(x - x_i(t))\delta(x - x') +}{\sum_{i \ne j} a_i a_j \delta(x - x_i(t))\delta(x' - x_j(t))}$$

$$= \dfrac{\delta(x - x')\sum_i a_i^2 \delta(x - x_i(t)) +}{\sum_{i \ne j} a_i a_j \delta(x - x_i(t))\delta(x' - x_j(t))} \text{ And}$$

$$= \dfrac{f_c^2(x, t)\delta(x - x') +}{\sum_{i \ne j} a_i a_j \delta(x - x_i(t))\delta(x' - x_j(t))}$$

$$f_c(x - x', t)f_c^*(x - x'', t) =$$

$$f_c^2(x - x', t)\delta(x' - x'') + \sum_{i \ne j} a_i a_j \delta(x - x' - x_i(t))\delta(x - x'' - x_j(t))$$

With wall-filtering (to remove stationary tissue, sometimes referred to as clutter-filtering) resulting in a sequence images with stationary tissue primarily rejected, the contrast ultrasound 3D HEX-ultrasound image is:

$$\tilde{g}_r(x, t)\tilde{g}_c^*(x, t) = (PSF_r(x) * f_c(x, t))(PSF_c(x) * f_c(x, t))^* =$$

$$\iint PSF_r(x')PSF_c(x'')f_c(x - x', t)f_c^*(x - x'', t)dx'dx'' =$$

$$\iint PSF_r(x')PSF_c(x'')f_c^2(x - x', t)\delta(x' - x'')dx'dx'' +$$

$$\iint PSF_r(x')PSF_c(x'')\sum_{i \ne j} a_i a_j \delta(x - x' - x_i(t))\delta(x - x'' - x_j(t))dx'dx'' =$$

$$\int PSF_r(x')PSF_c(x')PSF_c(x')f_c^2(x - x', t)dx' +$$

$$\sum_{i \ne j} a_i a_j \iint PSF_r(x')PSF_c(x'')\delta(x - x' - x_i(t))\delta(x - x'' - x_j(t))dx'dx''$$

But by the sifting property of the delta functions, the second term becomes:

$$\epsilon = \sum_{i \ne j} a_i a_j PSF_r(x - x_i(t))PSF_c(x - x_j(t))$$

But, if the agents are sparse such that the distance between any agents is much greater than the width of a PSF, then this term is negligible since the product of sufficiently separated PSFs is close to zero. Moreover, the scattering amplitudes and RF PSFs can be bipolar or even complex, thus the sum above may tend to a zero-average. Thus, we have:

$$\tilde{g}_r\tilde{g}_c^* \approx PSF_r(x)PSF_c(x) * f_c^2(x,t) + \epsilon = PSF_{rc}(x) * f_c^2(x,t) + \epsilon$$

Where $\epsilon$ is a ghost artifact residual. FIG. 13b depicts an example of the super-localization output with ghost artifacts. This represents the power of the sparse microbubble distribution as resolved by an improved row-column point-spread function plus some weak ghost artifacts that could be removed by thresholding or by a more intelligent algorithms as follows.

Ghost Artifact Removal Algorithm

For each detected contrast agent signature, check to see if there are agent signatures directly above and directly to the side in the an x-y image plane (for a fixed depth or projected to an xy-plane from a depth interval). If there are, then the contrast agent signature in question could be a ghost artifact. Discard the weakest signature then move to check the other agent signatures. FIG. 14a depicts a HEX-US image after ghost artifact removal.

Superlocalization and Super-Resolution

If the signal $PSF_{rc}(x) * f_c^2(x,t)$ is sufficiently distinct from the background, or if ghost artifacts can be sufficiently removed, then the agent signals may be super-localized by finding the centroids in the envelope-detected image and 3D super-resolution imaging can be performed by accumulating centroid positions over many observation times. FIG. 14b depicts a super-localization output.

Linear Scatterers

The Hadamard aperture coding and decoding assumes that the scatterers imaged are linear scatterers. However, microbubbles may be nonlinear scatterers. They may be sufficiently linear to implement the technique. The nonlinear components may not unmix appropriately and lead to artifacts but they will be weak and unfocused.

The scope of the following claims should not be limited by the preferred embodiments set forth in the examples above and in the drawings, but should be given the broadest interpretation consistent with the description as a whole.

What is claimed is:

1. A method for ultrasound imaging using a bias-switchable row-column array transducer having a plurality of row electrodes and a plurality of column electrodes that are not parallel to the row electrodes, the method comprising:
    performing one or more row transmit events, each transmit event comprising:
        identifying groups of row electrodes within the plurality of row electrodes;
        applying a bias voltage pattern to each group of row electrodes derived from an invertible matrix, the invertible matrix having positive and negative values;
        transmitting a waveform along each of the plurality of row electrodes, wherein, for a negative value of the invertible matrix, the waveform is inverted; and
        recording received column signals from the plurality of column electrodes;
    obtaining a column-acquired dataset for each of the groups of row electrodes using the received column signals from each of the one or more row transmit events;
    performing one or more transmit events, each transmit event comprising:
        identifying groups of column electrodes within the plurality of column electrodes;
        applying a bias voltage pattern to each group of column electrodes derived from an invertible matrix, the invertible matrix having positive and negative values;
        transmitting a waveform along each of the plurality of column electrodes; and
        recording received row signals from the plurality of row electrodes; and
    obtaining a column channel dataset for each of the groups of column electrodes using the received row signals; and
    generating an ultrasonic image based on the row channel data set and the column channel dataset.

2. The method of claim 1, wherein the groups of rows comprise multiple adjacent rows and/or the groups of columns comprise multiple adjacent columns.

3. The method of claim 1, wherein the invertible matrix is a Hadamard matrix.

4. The method of claim 1, wherein the invertible matrix is modified by a scalar.

5. The method of claim 1, wherein waveforms transmitted on adjacent rows and columns are scaled or delayed.

6. The method of claim 1, further comprising the steps of generating a row image from the row channel dataset, generating a column image from the column channel data set, and combining the row image and the column image to generate the ultrasonic image.

7. The method of claim 1, further comprising the steps of obtaining a plurality of row data sets and a plurality of channel data sets, generating a plurality of row images and column images, and combining and averaging the plurality of row images and column images to obtain a combined ultrasonic image.

8. The method of claim 7, wherein the row images and the column images are combined and averaged using phase information.

9. The method of claim 7, further comprising the step of applying temporal or spatio-temporal filtering over the plurality of row data sets and the plurality of channel data sets.

10. The method of claim 1, wherein the step of generating an ultrasonic image comprises applying a ghost artifact removal algorithm and/or a wall-filtering operation.

11. The method of claim 10, wherein the wall-filtering operation is an infinite impulse response filter, a finite impulse response filter, an eigenfilter, or a singular value decomposition filter.

12. The method of claim 1, wherein the ultrasonic image is a three-dimensional power Doppler image, a color Doppler image, a vector-flow image, a strain image, or a displacement-estimation image.

13. The method of claim 1, wherein the waveforms are transmitted to produce one of a plane wave, a cylindrically-diverging wave, or a cylindrically-converging wave.

14. The method of claim 1, further comprising the step of inputting the ultrasonic image into an algorithm for rendering, the algorithm for rendering comprising a generative adversarial network or cycle-consistent generative adversarial network trained on paired or unpaired data from another imaging modality.

15. The method of claim 1, further comprising the step of injecting ultrasound contrast agents into a specimen to be imaged.

16. The method of claim 15, further comprising the step of performing centroid localization of contrast agent signatures in the ultrasonic image.

17. The method of claim 16, wherein the step of performing centroid localization of contrast agent signatures is repeated to obtain a plurality of super-localization images, and the plurality of super-localization images being combined to form a super-resolution ultrasound image or a velocity image.

18. The method of claim 1, further comprising the step of applying an aperture decoding algorithm to at least one of the row channel data set and the column channel data set, the aperture decoding algorithm being based on an inverse of the invertible matrix.

19. The method of claim 1, further comprising the step of applying a beamforming algorithm or a reconstruction algorithm to at least one of the row channel data set and the column channel data set.

20. A system for ultrasound imaging comprising:
an array transducer having a plurality of row electrodes and a plurality of column electrodes that are not parallel to the row electrodes, the plurality of row electrodes being separated from the column electrodes by a dielectric layer;
a voltage source;
a signal generator;
a controller that is programmed with instructions to:
identify groups of row electrodes within the plurality of row electrodes and groups of column electrodes within the plurality of column electrodes;
perform one or more row transmit events by:
applying a bias voltage pattern to each group of row electrodes derived from an invertible matrix, the invertible matrix having positive and negative values;
transmitting a waveform along each of the plurality of row electrodes, wherein, for a negative value of the invertible matrix, the waveform is inverted; and
recording received column signals from each of the plurality of column electrodes;
obtain a row channel dataset for each of the groups of row electrodes using the received column signals;
perform one or more column transmit events by:
applying a bias voltage pattern to each group of column electrodes derived from an invertible matrix, the invertible matrix having positive and negative values;
transmitting a waveform along each of the plurality of column electrodes, wherein, for a negative value of the invertible matrix, the waveform is inverted; and
recording received row signals from each of the plurality of row electrodes;
obtain a column channel dataset for each of the groups of column electrodes using the received row signals; and
generate an ultrasonic image based on the row channel data set and the column channel dataset.

* * * * *